United States Patent [19]

Vivat et al.

[11] Patent Number: 4,927,921
[45] Date of Patent: May 22, 1990

[54] NOVEL 23-KETO-STEROIDS

[75] Inventors: Michel Vivat, Lagny-sur-Marne; Jean Buendia, Le Perreux-sur-Marne, both of France

[73] Assignee: Roussel Uclaf, Paris, France

[21] Appl. No.: 128,997

[22] Filed: Dec. 4, 1987

[30] Foreign Application Priority Data

Dec. 5, 1986 [FR] France .............................. 86 17051

[51] Int. Cl.$^5$ ............................................. C07J 9/00
[52] U.S. Cl. ..................... 540/110; 540/108; 552/549; 552/550; 552/551; 552/552; 552/548; 552/591; 552/554; 552/553
[58] Field of Search .............................. 260/397, 397.1

[56] References Cited

U.S. PATENT DOCUMENTS 3,455,910  7/1969  Fritsch et al. ................... 260/397.1
3,906,095  9/1975  Laurent et al. .................. 260/397.1
4,388,241  6/1983  Monks ............................. 260/397.1
4,500,460  2/1985  DeLuca et al. .

FOREIGN PATENT DOCUMENTS 900385 12/1984 Belgium .

OTHER PUBLICATIONS

Terasawa et al., "Synthesis of Cholesterol Analogs with a Carbene-Generating Substituent on the Side Chain", Chem. Pharm. Bull. 34(2), 931–934.
Ohtsuka et al., "Steroidal Inhibitors of Microbial Degradation of Sterol Side Chains", Chem. Pharm. Bull. 34(7), 2780–2785.
"Steroidal Inhibitors of Microbial Degradation of Sterol Side Chains", Ohtsuka et al., Chem. Abst. 107:134545 (1986).
"Synthesis of Cholesterol Analogs with a Carbene-Generated Substituent on the Side Chain", Terasawa et al., Chem. Abst. 105:209265 (1986).
"Synthesis of 23,23-Difluoro-25-Hydroxyvitamin D3", Taguchi et al., Chem. Abst. 102:149614 (1984).

Primary Examiner—H. M. S. Sneed
Assistant Examiner—J. Saba
Attorney, Agent, or Firm—Bierman and Muserlian

[57] ABSTRACT

A compound of the formula

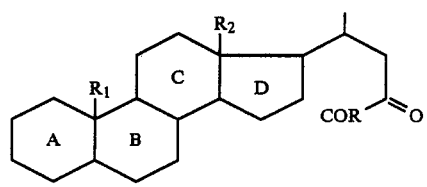

wherein $R_1$ is hydrogen or methyl, $R_2$ is methyl or ethyl, and A,B,C and D rings optionally containing at least one double bond and optionally substituted with at least one member of the group consisting of optionally protected —OH, =O, alkyl and alkoxy of 1 to 4 carbon atoms, halogen and alkenyl and alkynyl of 2 to 4 carbon atoms, R is selected from the group consisting of halogen, —OH, alkylthio and alkoxy of 1 to 6 carbon atoms, aralkoxy, arylthio and aralkylthio of 7 to 15 carbon atoms and

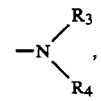

$R_3$ and $R_4$ are individually hydrogen, or alkyl of 1 to 6 carbon atoms or aralkyl of 7 to 15 carbon atoms or taken together with the nitrogen form a heterocycle optionally containing another nitrogen or oxygen atom, excepting the product in which R is methoxy, $R_1$ and $R_2$ each represent methyl, A ring carries a 3β-acetoxy function and B ring contains a double bond in 5(6) useful as intermediates for the preparation of 20-keto-pregnanes.

7 Claims, No Drawings

23-KETO-STEROIDS

STATE OF THE ART

Related prior art includes U.S. Pat. No. 4,500,460; No. 2,445,006; No. 2,495,735 and No. 2,180,095 and JACS, Vol. 74 (1952), p. 5814–5817.

OBJECTS OF THE INVENTION

It is an object of the invention to provide the novel compounds of Formula I and a process for their preparation.

It is another object of the invention to provide a novel process for the preparation of 20-keto-pregnanes and novel intermediates formed therein.

These and other objects and advantages of the invention will become obvious from the following detailed description.

THE INVENTION

The novel compounds have the formula

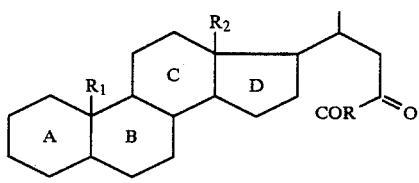

I wherein $R_1$ is hydrogen or methyl, $R_2$ is methyl or ethyl, the A, B, C and D rings optionally containing at least one double bond and optionally substituted with at least one member of the group consisting of optionally protected —OH, =O, alkyl and alkoxy of 1 to 4 carbon atoms, halogen and alkenyl and alkynyl of 2 to 4 carbon atoms, R is selected from the group consisting of halogen, —OH, alkylthio and alkoxy of 1 to 6 carbon atoms, aralkoxy, arylthio and aralkylthio of 7 to 15 carbon atoms and

$R_3$ and $R_4$ are individually hydrogen, or alkyl of 1 to 6 carbon atoms or aralkyl of 7 to 15 carbon atoms or taken together with the nitrogen form a heterocycle optionally containing another nitrogen or oxygen atom, excepting the product in which R is methoxy, $R_1$ and $R_2$ each represent methyl, A ring carries a 3β-acetoxy function and B ring contains a double bond is 5(6).

When the A, B, C and D rings carry at least one double bond, it is preferred for the double bonds to be at 1(2), 4(5), 5(6) or 9(11) or for a system of conjugated double bonds at 3(4) and 5(6) or at 4(5) and 6(7) or for an aromatic system of three double bonds 1, 3, 5, or for a system of three double bonds 1(2), 4(5), 6(7). However, it is preferred to use products which do not include double bonds. When the A, B, C and D rings are substituted by at least one hydroxyl, it is preferred for there to be hydroxyls at 3, 6, 7, 11 and/or 12. When the A, B, C and D rings are substitued by at least one ketone, it is preferred for there to be a ketone function at 3, 7, 11 or 12.

When the A, B, C and D rings are substituted by at least one halogen, it is preferred for there to be a fluorine, chlorine or bromine atom at position 6 or 9α-, for example. When the A, B, C and D rings are substituted by at least one alkyl, it is preferred for methyl or ethyl to be 2, 6, 7, or at 16α- or 16β-. When the A, B, C and D rings are substituted by at least one alkyloxy, it is preferred for methoxy or ethoxy at 3 or 11β-. When the A, B, C and D rings are substituted by at least one alkenyl, it is preferably vinyl or allyl in position 11β-, for example. When the A, B, C and D rings are substituted by at least one alkynyl, it is preferably ethynyl in 11β-position, for example.

The hydroxyl groups can be protected in the usual ways known in the literature. There can be cited, for example, acetonides, cyclic carbonates, orthoesters, cyclic sulfites, ether formed with tetrahydropyrannyl, trityl or benzyl and acyls such as acetyl, succinyl or formyl.

The ketone groups can also be protected by standard protector groups such as ketals, more specially ethylene ketal, thioacetals, hemithioacetals, enol ethers, enol acetates, enamines and oximes. However, ketal groups are preferred, especially ethylene ketal, to protect the ketones. When the products of Formula I have a 3-ketone group, this group is very preferentially protected.

R may be a halogen, preferably chlorine or bromine; R may be alkoxy preferably methoxy or ethoxy, but also propyloxy, isopropyloxy, butyloxy, sec-butyloxy, tert-butyloxy, pentyloxy, or hexyloxy; benzyloxy or phenethoxy.

$R_3$ and $R_4$ can individually be hydrogen or methyl, ethyl, propyl, isopropyl, butyl, sec-butyl, tert-butyl, pentyl, hexyl or benzyl, or $R_3$ and $R_4$ together with the nitrogen atom to which they are bonded form morpholine, piperidine or pyrrolidine. R may also be methylthio or ethylthio or alkylthio derived from the alkyls or alkoxys indicated above as well as phenylthio or benzylthio.

The preferred products of Formula I are those wherein $R_1$ and $R_2$ are methyl, and the A, B, C and D rings carry an optionally protected 3-hydroxyl and, optionally at least one other function chosen from the optionally protected hydroxyl functions in the 6, 7, 11 and 12 positions, and the optionally protected ketone in position 7, 11 and 12, and R is hydroxy alkoxy of 1 to 4 carbon atoms, or

wherein $R'_3$ and $R'_4$ are hydrogen, alkyl of 1 to 4 carbon atoms or $R'_3$ and $R'_4$ together with the nitrogen atom to which they are bonded form piperidino, pyrrolidino or morpholino and more especially, the products of Formula I wherein the A, B, C and D rings carry at position 3 an optionally protected hydroxyl and optionally at least one other function chosen from optionally protected 12-hydroxyl and optionally protected 11- or 12-ketone and R is hydroxyl, methoxy or ethoxy, or morpholino.

Other preferred products are particularly advantageous the sub-family of products constituted by the products of Formula I wherein the A, B, C and D rings carry an optionally protected 3-hydroxyl, and optionally at least one other function chosen from optionally protected hydroxyl functions in position 6, 7 or 12 and optionally protected ketone in position 7, 11 or 12.

In the last family, there can be cited the products including, as skeleton of the rings A, B, C and D, products derived from the natural or semi-synthetic biliary acids which products are enumerated in the following table:

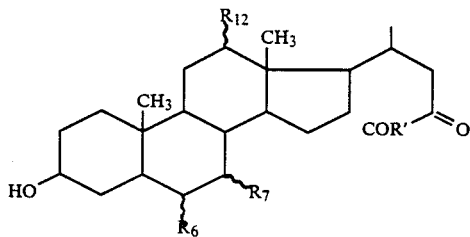

wherein R' is hydroxyl, methoxy, ethoxy or morpholino, and $R_6$ $R_7$ and $R_{12}$ have the following significances:

| $R_6$ | $R_7$ | $R_{12}$ |
|---|---|---|
| H | α-OH | α-OH |
| H | β-OH | α-OH |
| H | H | H |
| H | H | α-OH |
| H | α-OH | H |
| α-OH | H | H |
| H | β-OH | H |
| α-OH | α-OH | H |
| β-OH | α-OH | H |
| β-OH | β-OH | H |
| H | H | α-OH |
| H | α-OH | α-OH |

In these products, the hydroxyls may also be protected, notably the 3-hydroxyl. The preferred protector group is acetyl or formyl.

Among the products including at least one ketone, the following products are preferred:

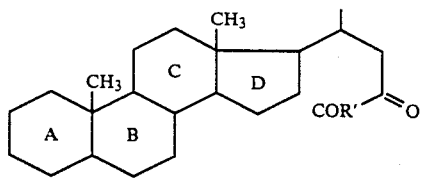

wherein R' is hydroxyl, methoxy, ethoxy or morpholino and the substituents in position 3, 7, 11 and 12 have the following significances:
 3 protected ketone
 -13α-OH, 7-keto, 12α-OH
 -3α-OH, 11-keto
 -3α-OH, 7α-OH, 12-keto
 -3α-OH, 7-keto
 -3α-OH, 7β-OH, 12-keto
 -3-OH, 11-keto, 12-OH
 3-OH, 11-keto.

Naturally, the hydroxyls may be protected and the same applies to the ketones in position 7 or 12. The preferred protector group for the ketone group is a cyclic or non-cyclic ketal.

Specific preferred compounds of the invention are 4-[3α-acetyloxy-5β-cholan-11,23,24-trione-24-yl]-morpholine, 5β-cholan-3α-ol-11,23-dione-24-oic acid, the methyl ester of 5β-cholan-3α-ol-11,23-dione-24-oic acid and 3α-acetoxy-5β-cholan-11,23-dione-24-oic acid.

The novel process of the invention for the preparation of a compound of Formula I comprises reacting a compound of the formula

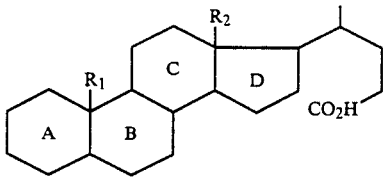

II wherein A, B, C, D, $R_1$ and $R_2$ have the above definition with a reagent to form the halide, then with a tertiary base, then with thionyl chloride and optionally then with a member of the group consisting of water, alkanol, or aralkanol, alkylthiol, arylthiol, aralkylthio, or

wherein $R_3$ and $R_4$ have the above definition to form a compound of the formula

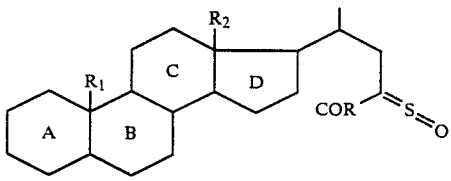

III wherein A, B, C, D, R, $R_1$ and $R_2$ have the above definition and reacting the latter either (a) with an aqueous acid or an oxidant or (b) with a halogenation reagent, then with a basic hydrolysis agent and where R is —OH, optionally reacting the product with a reactant to form the acid halide, alkanol, aralkanol, alkylthiol, arylthiol, aralkylthiol or

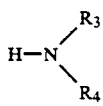

wherein $R_3$ and $R_4$ have the above definition, to obtain the corresponding compound of Formula I.

In a preferred mode of the invention, the reagent of the formation of the acid halide is oxalyl chloride or oxalyl bromide and most preferably, thionyl chloride.

The tertiary base used is chosen from triethylamine, methylethyl-pyridine, pyridine, diazabicyclo-octane, diazabicyclo-nonene, diazabicyclo-undecene, and preferably triethylamine or pyridine. The preferred alkanol or aralkanol is methanol, ethanol or benzyl alcohol. The primary or secondary amine used is chosen from methyl- or ethylamine, diethylamine, morpholine, piperidine, pyrrolidine, and preferably morpholine. Naturally, the corresponding thiol can be used. The alkylthiol, arylthiol or aralkylthiol used is chosen preferably from methanethiol, ethanethiol and thiobenzyl alcohol. The preferred aqueous acid to convert the products of Formula III into products of Formula I is sulfuric acid, but another mineral or organic acid such as hydrochloric acid or acetic acid can also be used.

When an oxidant is used, it may be potassium permanganate, hydrogen peroxide, ozone, a perborate or a persulfate. Generally, the action of an aqueous acid or an oxidant on the products of Formula III leads to a product of Formula I in which R is hydroxyl. If necessary and if desired, other products of Formula I can then be prepared for example, by reacting an alkanol such as methanol separately or simultaneously to obtain a product of Formula I in which R is alkoxy or a primary or secondary amine such as morpholine to obtain the products of Formula I in which R is

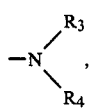

as well as the corresponding thiols. In a preferred way, acid hydrolysis or oxidation is carried out in the presence of the alkanol or the primary or secondary amine of which it s desired to obtain the derivative of Formula I.

Naturally, an agent for an acid halide chosen from the list indicated above can also be made to act on a product of Formula I in which R is —OH. The reactions mentioned above for the preparation of products of Formula III can preferably be carried out in a solvent or a mixture of solvents miscible slightly or not at all with water such as methylene chloride, and chloroform.

The standard blocking or unblocking reactions for the functional groups optionally on the rings A, B, C and D can be carried out at the beginning of the synthesis, on the products of Formula II or on the products obtained of formula I. For example, the products of Formula I in which the A ring includes a 3-hydroxyl protected by an acyl such as acetyl or formyl can be submitted to a standard saponification reaction to obtain the corresponding product in which the A ring has a free hydroxyl. The operation is done by the usual methods by reaction, for example, of a base such as sodium hydroxide, potassium hydroxide or potassium carbonate in a solvent such as methanol, methylene chloride, water or a mixture of such solvents.

Inversely, the products of Formula I can also be submitted to the action of a derivative of a protector group such as acetic anhydride to protect a free hydroxyl, for example in the 3-position.

Another object of the invention is a process for the preparation of a compound of the formula

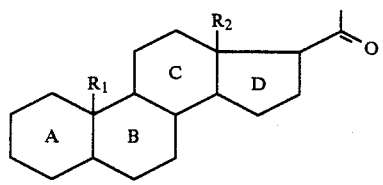

wherein A, B, C, D, $R_1$ and $R_2$ have the above definitions comprising reacting a compound of Formula I with a strong oxidizing agent to obtain a compound of the formula

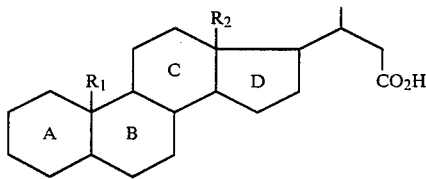

reacting the latter with a reagent to form the acid halide and reacting the latter with a tertiary base and then thionyl chloride and then optionally with a member of the group consisting of water, alkanol, aralkanol, alkylthiol, arylthiol, aralkylthiol and

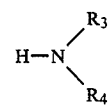

wherein $R_3$ and $R_4$ have the above definition to obtain a compound of the formula

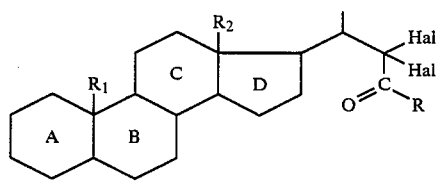

wherein A, B, C, D, R, $R_1$ and $R_2$ have the above definition and Hal is halogen and reacting the latter with a dehydrohalogenation reagent and then an oxidizing cleavage agent to obtain the corresponding compound of Formula VI.

The strong oxidizing agent may be Jones' reagent (chromic and sulfuric acid in water), lead tetra acetate, hydrogen peroxide and potassium dichromate.

The agent for formation of an acid halide is chosen from the list indicated above, preferably thionyl chloride. The other reagents are also chosen from the lists above. The halogenation reagent is a halogen such as bromine or a halogenation reagent such as sulfuryl chloride. The deshydrohalogenation agent is preferably a strong basic agent such as Triton B,

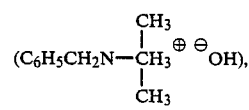

an alkali metal alcoholate such as sodium or potassium ethanolate, potassium tert-butylate or a sodium or potassium amide. Utilizing a base such as sodium or potassium hydroxide at reflux in an alkanol such as methanol or ethanol or glyme is also possible or a basic resin such as Amberlite. The oxidizing cleavage agent is chosen from ozone and an oxidant such as ruthenium oxide or manganese oxide.

The action of a dehydrohalogenation reagent on the products of Formula V gives rise to a product of the following formula

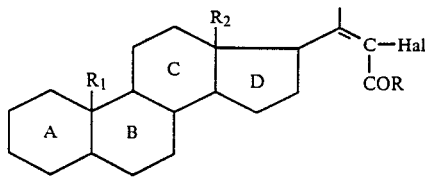

which product is then able, after oxidizing cleavage, to lead to the products of the Formula VI.

Natually, in the preparation of the products of Formula VI, the standard reactions of blocking and unblocking the functional groups which the rings A, B, C and D may include can be carried out either on the starting products of Formula I or on the intermediate products of the synthesis.

Especially, in the case where the dehydrohalogenation reaction carried out on the intermediate products of Formula V leads to a saponification of the acyl protector group such as acetyl or formyl, the product having a free hyroxyl may be re-acylated by means, for example, of acetic anhydride in the presence of pyridine.

Also, the processes described above, the formation agent of an acid halide is thionyl chloride.

As the formation reaction of the sulfine function includes the use of thionyl chloride, the linking together of the reagents indicated above, namely:

(a) action of a formation agent of an acid halide,
(b) tertiary base, then
(c) thionyl chloride, in the preferred form where the formation agent of an acid halide is thionyl chloride, amounts to the action on the product of Formula II of thionyl chloride in the presence of a tertiary base. Finally, the products of Formula V are a subject of the invention, as new industrial products and especially as industrial products for the utilization of the products of Formula I.

The starting products of Formula II are known products, for many of the natural products of the biliary acid series, or of the products which can be prepared by the usual methods starting with these natural products.

The products of Formula VI are products of the progesterone series and these products possess interesting pharmacological properties. Furthermore, thes products can serve as starting material for the reconstruction of the deoxycortisone chain

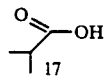

or for other chains in the position 17.

In the following examples, there are described several preferred embodiments to illustrate the invention. However, it is to be understood that the invention is not intended to be limited to the specific embodiments.

EXAMPLE 1

5β-cholan-3α-ol-11,23-dione-24-oic acid

Step A: 3α-acetyloxy-5β-cholan-11-one-24-oic acid 200 g of 5β-cholan-3α-ol-11-one-24-oic acid and 400 ml of acetic anhydride are mixed together and the mixture was heated to 45° C. 2 g of p-toluene sulfonic acid and 20 ml of acetic acid were introduced all at once and the temperature rose to 63° C. in 5 minutes. The mixture was kept at 60° C. for one hour and then was brought down to 55° C. Over about 1 hour, 400 ml of distilled water were added at +55° C. and after cooling to +10° C., the precipitate formed was separated, washed and dried under reduced pressure to obtain 211 g of 3α-acetyloxy-5β-cholan 11-one-24-oic acid melting at 225° C. (purity near to 99%).

106 g of the product obtained were dissolved in methylene chloride, filtered on silica and eluted with a mixture of methylene chloride and ethyl acetate (9/1) to obtain 105 g of purified product melting at 225° C.

I.R. Spectrum (chloroform in cm$^{-1}$)

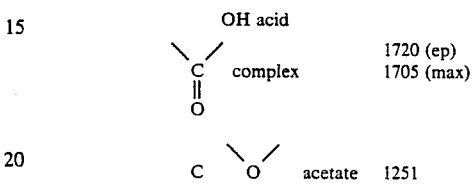

NMR Spectrum (CDCl$_3$) in ppm.

| H of CH$_3$ at position 18 | 0.62 | H of ACO | 2.03 |
|---|---|---|---|
| H of CH$_3$ at position 21 | 0.88–0.93 | H in position 3 | 4.72 |
| H of CH$_3$ at position 19 | 1.2 | H of COOH | 8.71 |

Stage B:
4-[3α-(acetyloxy)-11,23,24-trioxo-5β-cholan-24-yl)-morpholine

Under an inert atmosphere, 68 g of the product of Step A, 250 ml of methylene chloride and 0.35 ml of N,N-dimethylformamide were mixed together and at reflux of the methylene chloride, 12.8 ml of thionyl chloride were added over about 15 minutes. Reflux was maintained for 45 minutes, followed by concentration to dryness by distilling under reduced pressure. 250 ml of methylene chloride were added to the crystallized acid chloride and at −15° C., 12.8 ml of thionyl chloride were added. At −25° C. and over about 90 minutes, a mixture of 46.5 ml of triethylamine and 46.5 ml of methylene chloride were added, and the suspension was stirred for 30 minutes. While maintaining the temperature at −25° C. and over about 30 minutes, a mixture of 35.5 ml of morpholine and 50 ml of methylene chloride were added, with stirring for thirty minutes. Then, over about 10 minutes, 350 ml of water were added, while allowing the temperature to rise towards 0° C. 4.7 ml of acetic acid were added, and at +2° C./+5° C., over about 90 minutes, 49.6 g of potassium permanganate were added. The mixture was diluted during this introduction with 240 ml of water, and stirring was maintained to +2°/+5° C. for one hour. At +5°/+10° C. and over about 30 minutes, 43 g of sodium bisulfite, and simultaneously, a solution of 12 ml of concentrated sulfuric acid in 150 ml of iced water were added. After decanting, the methylene chloride phase was washed with water and dried, and 5 g of magnesium sulfate and then 60 g of aluminium CBT$_1$ were added under good stirring at 20° C. for 90 minutes. Stirring was maintained for a further 90 minutes at ambient temperature, then after filtering, the filtrate was concentrated to dryness by distilling under reduced pressure. 80 ml of ethyl acetate were added to the residue, followed by concentrating to dryness by distilling under reduced pressure to expel the residual methylene chloride, and 100 ml of ethanol were added to the residue. Solution occurred by stirring at about 40° C. and then the solution was cooled to 0° C., and crystallization was initiated. After standing for 16 hours, 57.6 g of -4-[3α-(acetyloxy)-11,23,24-trioxo-5β-cholan-24-yl)-morpholinne melting at 122°–123° C. were obtained. The mother liquors were concentrated to dryness, and a residue of 22 g titrating 83.5% of the expected product were obtained.

IR Spectrum (chloroform) in cm$^{-1}$.

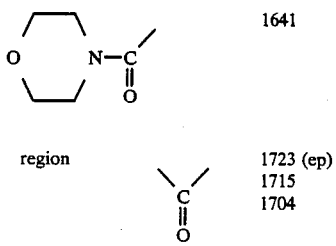

NRM Spectrum (CDCl$_3$) in ppm.

| | |
|---|---|
| H of CH$_3$ in position 18 | 0.67 |
| H of CH$_3$ in position 21 | 0.9–1.0 |
| H of CH$_3$ in posiiton 19 | 1.17 |
| H of ACO | 2.0 |
| H in position 3 | 4.7 |
| H of the morpholine | 3.4–3.8 |

STEP C: 5β-cholan-3α-ol-11,23-dione-24-oic acid

Under an inert atmosphere, 0.5 g of the product of Step B, 5 ml of methanol with 5% of water, and 0.75 g of sodium hydroxide in pastilles were mixed together and left for 24 hours at ambient temperature. The solution became clear, and a 2N aqueous solution of hydrochloric acid was added until the pH showed acid, then extraction was done with ethyl acetate. The extracts were dried, concentrated to dryness by distilling under reduced pressure to obtain 0.4 g of 5β-cholan-3α-ol-11,23-dione-24-oic acid.

IR Spectrum (chloroform) in cm$^{-1}$

| 3 | hydroxy OH | 3605 | Region C=O | 1781 |
|---|---|---|---|---|
| 3 | forms of acid | 3410 | ep | 1750 |
| | | 1781 | | 1700 |
| | | 3510 monomer | | 1710 |
| | | | | 1703 |

EXAMPLE 2

5β-cholan-3α-ol-11,23-dione-24-oic acid

Stage A:
3α-formyloxy-23-sulfinyl-5β-cholan-11-one-24-oic acid 83.7 g 3α-formyloxy-23-sulfinyl-5β-cholan-11-one-24-oic acid, 840 ml of methylene chloride and 168 ml of pyridine were mixed together, cooled to +10° C., and over about 5 minutes while allowing the termperature to rise to +20° C., 32 ml of thionyl chloride were introduced. After stirring at 20° C. for one hour, over about 5 minutes, 84 ml of water were added with stirring at 20° C. for 15 minutes. The reaction mixture was then poured into an iced aqueous solution of hydrochloric acid, and after stirring, then decanting, extraction was done with methylene chloride. The extracts were treated with active charcoal, then concentrated to dryness by distilling under reduced pressure to obtain 98.5 g of the crude expected product with an Rf.=0.45 [eluting with a mixture of chloroform, isopropanol and acetic acid (85/14/1)].

Analysis: C$_{25}$H$_{36}$O$_6$S; molecular weight 464.60 Calculated: C% 64.82 H% 7.81 S% 6.90 Found: 64.8 7.7 7.00

UV Spectrum (ethanol).
Max. at 282 nm. E$^1$$_1$=157 ε=6400 that is −77% in sulfine.

Step B: Methyl ester of
5β-cholan-3α-ol-11,23-dione-24-oic acid

Under an inert atmosphere, 2 g of the product of Step A, 20 ml of methanol and 0.4 ml of concentrated sulfuric acid were mixed together and refluxed for 2 hours, then poured into a mixture of water and ice, and extracted with ethyl acetate. The extracts were washed with water, dried and concentrated to dryness by distilling under reduced pressure. The residue was chromatographed on silica and eluted with a mixture of methylene chloride and ethyl acetate (9/1) to obtain 0.64 g of product which was crystallized from a mixture of methylene chloride and isopropyl ether, to obtain methyl ester of 5β-cholan-3α-ol-11,23-dione-24-oic acid melting about 75° C. with an Rf.=0.32 [eluting with a mixture of methylene chloride and ethyl acetate (85/15)].

IR Spectrum (chloroform)

Absence of formate—Presence of OH, ketone not conjugated and ester band wide.

H of position 18 Me.: 0.67
H of position 20 Me.: 0.9–1.0
H of position 19 Me.: 1.14
H$_3$: 3.67
H of COOCH$_3$: 3.9

Step C: 5β-cholan-3-ol-11,23-dione-24-oic acid

Under an inert atmosphere, 0.5 g of the product of Step C, 5 ml of methanol, 1.3 ml of water, and 135 mg of sodium hydroxide in pastilles were mixed together and stirred at 20° C. for 20 hours. The reaction mixture was then poured into a mixture of N hydrochloric acid and ice, and after stirring, the precipitate formed was separated, washed with water, dissolved in methylene chloride, dried, concentrated to dryness by distilling under reduced pressure to obtain 0.43 g of 5β-cholan-3α-ol-11,23-dione-24-oic acid.

IR Spectrum (chloroform) in cm$^{-1}$.

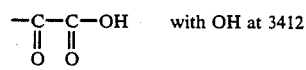
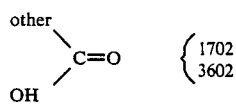

EXAMPLE 3

5β-cholan-3α-ol-11,23-dione-24-oic acid

Step A:
3α-formyloxy-22,23-dibromo-5β-cholan-11-one-24-oic acid

Under an inert atmosphere, 20.9 g of 3α-formyloxy-5β-cholan-11-one-24-oic acid, 200 ml of methylene chloride and 32 ml of pyridine were mixed together and over about 5 minutes at +5° C. and while allowing the temperature to rise to +20° C., 8 ml of thionyl chloride were added with stirring at 20° C. for 1 hour, followed by cooling to 10° C. Over about 5 minutes, 8 ml of bromine were introduced and the mixture was stirred at 20° C. for one hour. The reaction mixture was poured into a mixture of water and ice, stirred, decanted, and extracted with methylene chloride. The extracts were dried, treated with active charcoal with a little aluminum, filtered and concentrated to dryness by distilling under reduced pressure. 40 ml of formic acid were added to the residue, and after heating to boiling point for 5 minutes, the formic acid was eliminated by distilling under reduced pressure. 40 ml of isopropyl ether were added slowly, and after cooling, 24.6 g of 3α-formyloxy-22,23-dibromo-5β-cholan-11-one-24-oic acid melting at 248° C. and with a Rf.=0.40 [eluting with a mixture of chloroform, isopropanol and acetic acid (85/14/1)] were obtained.

Analysis: $C_{25}H_{36}O_5Br_2$ molecular weight=576.38
Calculated: C% 52.09 H% 6.30 Br% 27.73 Found: 52.0 6.3 27.4

Step B: 5β-cholan-3α-ol-11,23-dione-24-oic acid

Under an inert atmosphere, 46.6 g of the product of Step A and 930 ml of N sodium hydroxide were mixed together and the suspension was heated at 100° C. for 4 hours. After cooling, ice was added, then 100 ml of hydrochloric acid, followed by concentrating and extracting with ethyl acetate. The extracts were dried, treated with active charcoal with a little aluminum, then filtered, and the filtrate was concentrated to dryness by distilling under reduced pressure. Methylene chloride was added to the residue, and crystallization took place to obtain 25.4 g of 5β-cholan-3α-ol-11,23-dione-24-oic acid melting at about 155° C.

The product was chromatographed on silica and eluted with a mixture of chloroform, isopropanol and acetic acid (80/18.5/1.5). The interesting fractions were concentrated and ethyl acetate was added. After washing with water, drying, and concentrating to dryness by distilling under reduced pressure, they were crystallized from a mixture of acetone and petroleum ether (b.p.=60° to 80° C.) to obtain the desired product melting at 130° C. with a Rf.=0.35 [eluting with a mixture of chloroform, isopropanol and acetic acid 78/20/2].

IR Spectrum (chloroform).
Presence of OH, 11-keto, and

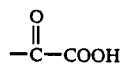

NMR Spectrum (CDCl₃) in ppm.
H of position 18 Me: 0.68
H of position 20 Me: 0.9–1.0
H of position 19 Me: 1.18
Mobile H's: 4.4

EXAMPLE 4

3α-(acetyloxy)-5β-cholan-11,23-dione-24-oic acid

Under an inert atmosphere, 141 mg of 5β-cholan-3α-ol-11,23-dione-24-oic acid, 0.3 ml of acetic anhydride, and 3 mg of toluene sulfonic acid were mixed together and stirred for a further 15 minutes. After extracting with ethyl acetate, the extracts were washed with water, dried, and concentrated to dryness by distilling under reduced pressure. The residue was chromatographed on silica nd eluted with a mixture of methylene chloride, isopropanol and acetic acid (87-12.5-0.5) to obtain 80 mg of 3α-(acetyloxy)-5β-cholan-11,23-dione-24-oic acid IR Spectrum (chloroform), in cm⁻¹.

EXAMPLE 5

3α-acetoxy-5β-pregnane-11,20-dione

Stage A:
3α-(acetyloxy)-24-nor-5β-cholan-11-one-23-oic acid

Under an inert atmosphere, 893 mg of 3-(acetyloxy)-5-cholan-11,23-dione-24-oic acid and 6 ml of acetic acid were mixed together, and at +15° C., over about 20 minutes, 4.5 ml of Jones' oxidizing solution (prepared from 267 g of $CrO_3$, 230 ml of $H_2SO_4$ and water to 1000 ml) were introduced with stirring at +15° C. for 5 minutes. The reaction mixture was poured into iced water, and extracted with methylene chloride. The extracts were washed with a 0.1M aqueous solution of sodium thiosulfate, then with water, dried, and concentrated to dryness by distilling under reduced pressure. The residue was chromatographed on silica and eluted with a mixture of methylene chloride and acetone 9/1 to obtain 680 ml of impure 3α-(acetyloxy)-24-nor-5β-cholan-11-one-23-oic acid melting at 110°–120° C.

IR Spectrum (chloroform)
Presence of acetate, 11-oxo and acid.
NMR Spectrum (CDCl₃) in ppm.
H of position 18 Me: 0.66
H of position 21 Me: 0.97–1.02
H of position 19 Me: 1.18
H of ACO: 2.0
H₃: 4.68

Step B:
4-[3α-(acetyloxy)-22,22-dibromo-11-oxo-24-nor-5β-cholan-23-yl)]-morpholine Under an inert atmosphere, 4.1 g of the product of Step A, 41 ml of methylene chloride and 6.35 ml of pyridine were mixed together, and at 0°/+5° C., 1.57 ml of thionyl chloride were added. Then immediately 1.6 ml of bromine were added with stirring at 20° C. for one hour. At 0°/−5° C., over about 15 minutes, 8.5 ml of morpholine were added with stirring for 1 hour, while allowing the temperature to return to 20° C. The reaction mixture was poured into 400 ml of 2N iced hydrochloric acid and was extracted with chloroform.

The extracts were washed with water, dried, concentrated to dryness by distilling under reduced pressure. The 6.5 g of residue were chromatographed on silica and eluted with a mixture of cyclohexane and ethyl acetate (8/2) to obtain 2.075 of 4-[3α-(acetyloxy)-22,22-dibromo-11-oxo-24-nor-5β-cholan-23-yl)]-morpholine.

IR Spectrum (chloroform) in cm$^{-1}$.

| OAC | 1724 |
|---|---|
|  | 1364 |
| C—O complex | 1267–1251–1235 |
| 11-oxo | 1704 |
| amide | 1645 |

NMR Spectrum (CDCl$_3$) in ppm.
H of position 18 Me: 0.74
H of position of 19 Me: 1.16
H of position 21 Me: 1.34–1.42
H of ACO: 1.8
H of the morpholine: 3.76
H$_3$: 4.7
Analysis: C$_{29}$H$_{43}$Br$_2$NO$_5$; molecular weight=645.48
Calculated: C% 53.96 H% 6.71 N% 2.17 Br% 24.76
Found: 53.9 6.7 2.1 24.6

Step C: 3α-acetoxy-5β-pregnane-11,20-dione 1° Debromohydration

Under an inert atmosphere, 250 mg of the product of Step B, 2.5 ml of methanol, and 2.5 ml of triton B (or benzyl trimethyl ammonium hydroxide) at 40% in aqueous solution were mixed together and refluxed for 1 hour. After cooling, the reaction mixture was poured into iced water, and extracted with methylene chloride. The extracts were washed with water, dried and concentrated to dryness by distilling under reduced pressure to obtain 120 mg of 3α-acetoxy-5β-pregnane-11,20-dione, which was used as is for the following reaction.

2°. Acetylation.

Under inert atmosphere, the said product, 1.2 ml of pyridine and 0.48 ml of acetic anhydride were mixed together and left in contact for 20 hours. The mixture was then poured into iced water, and after 30 minutes, was extracted with methylene chloride. The extracts were washed with water, dried, and concentrated to dryness by distilling under reduced pressure to obtain 170 mg of the expected acetylated product which was used as is for the following reaction.

3°. Ozonolysis

Under an inert atmosphere, the acetylated product, 2.5 ml of 1,2-dichlorethane, and 1 ml of acetic acid were mixed together, and at −5° C., a current of ozonized oxygen was passed for 15 minutes. The excess of ozone was eliminated by bubbling nitrogen through and then the reaction mixture was poured slowly into an excess of an aqueous solution of sodium bicarbonate. Extraction was done with methylene chloride and the extracts were washed with water, dried and concentrated to dryness by distilling under reduced pressure to obtain 115 mg of 3α-acetoxy-5β-pregnane-11,20-dione. The crude product was chromatographed on silica and eluted with a mixture of cyclohexane and ethyl acetate (8/2) to obtain 16 mg of the purified product, of which the infra-red spectrum was identical to that of an authentic sample.

EXAMPLE 6

3α-acetoxy-5β-pregnane-11,20-dione

1° Bromination.

Under an inert atmosphere, 3.2 g of 3α-acetoxy-24-nor-5β-cholan-11-one-23-oic acid (titer 85%) from Stage A of example 5, 32 ml of methylene chloride and 6.1 ml of pyridine were mixed together, and at −5° C., over about 10 minutes, 1.2 ml of thionyl chloride were added dropwise. Then, at −10° C. over 10 minutes, 0.6 ml of bromine were added and after stirring for 150 minutes at 20° C., 8 ml of diethylamine were introduced at −5° C. over about 20 minutes. The mixture was stirred for 1 hour at 20° C. and then was poured into 2N iced hydrochloric acid with stirring for 15 minutes. Extraction was done with methylene chloride and the extracts were washed with water, dried, treated with active charcoal, and taken to dryness by distilling under reduced pressure to obtain 5.1 g of crude brominated product which was used as is for the following reaction.

2° Treatment with Triton B (debromohydration)

Under an inert atmosphere, 1.5 g of the crude brominated product, 15 ml of methanol and 12 ml of Triton B (benzyl trimethyl ammonium hydroxide) at 40% in aqueous solution were mixed together and refluxed for 90 minutes, then cooled, poured into water, and extracted with methylene chloride. The extracts were washed with water saturated with sodium chloride, with a 0.5M aqueous solution of monosodium phosphate, and with water saturated with sodium chloride, then dried and concentrated to dryness by distilling under reduced pressure to obtain 837 mg of crude product which was used as is for the following reaction.

3°. Acetylation

Under an inert atmosphere, the 837 mg of said product, 3 ml of pyridine and 1.5 ml of acetic anhydride were mixed together and stirred at 20° C. for 20 hours. A few ml of water were added, and after stirring for 1 hour, the reaction mixture was poured into water saturated with sodium chloride, and extracted with methylene chloride. The extracts were washed with water saturated with sodium chloride, dried, and concentrated to dryness by distilling under reduced pressure to obtain 954 mg of crude acetylated product which was used as is for the following reaction.

4°. Ozonization.

The 954 mg of crude acetylated product, 15 ml of methylene chloride and 8 ml of acetic acid were mixed together, and at 0° C., a current of ozonized oxygen was passed for 1 hour. Then, the reaction mixture was poured into water and extracted with methylene chloride. The extracts were washed with water saturated with sodium chloride, dried, and concentrated to dryness by distilling under reduced pressure to obtain 992 mg of crude ozonized product. The crude product was chromatographed on silica and eluted with a mixture of cyclohexane and ethyl acetate (75/25) to obtain 106 mg of 3α-acetoxy-5β-pregnane-11,20-dione.

IR Spectrum (chloroform)

The spectrum was identical to that of an authentic sample of 3α-acetoxy-11,20-dioxo-5β-pregnane.

Various modifications of the products and processes of the invention may be made without departing from the spirit or scope thereof and it should be understood that the invention is intended to be limited only as defined in the appended claims.

What we claim is:

1. A compound of the formula

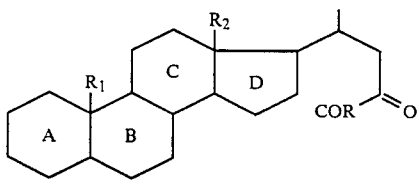

I wherein $R_1$ is hydrogen or methyl, $R_2$ is methyl or ethyl, the A, B, C and D rings saturated or containing at least one double bond and substituted with at least one member of the group consisting of 12-OH, protected 12-OH, 11 or 12=O, 11- or 12-protected keto, R is selected from the group consisting of halogen, —OH, alkylthio and alkoxy of 1 to 6 carbon atoms, aralkoxy, arylthio and aralkylthio of 7 to 15 carbon atoms and

$R_3$ and $R_4$ are individually hydrogen or alkyl of 1 to 6 carbon atoms or aralkyl of 7 to 15 carbon atoms or taken together with the nitrogen form a heterocycle, which may contain another nitrogen or oxygen atom excepting the product in which R is methoxy, $R_1$ and $R_2$ each represent methyl, A ring carries a 3β-acetoxy function and B ring contains a double bond in 5(6).

2. A compound of claim 1 wherein $R_1$ and $R_2$ are methyl and the A, B, C and D rings contain an 3-OH or protected 3-OH and contain OH or protected —OH in the 6, 7, 11 and/or 12-positions and keto or protected keto in the 7, 11 and/or 12-positions and R is selected from the group consisting of —OH, alkoxy of 1 to 4 carbon atoms and

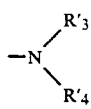

and $R'_3$ and $R'_4$ are hydrogen or alkyl of 1 to 4 carbon atoms or together with the nitrogen form piperidino, pyrrolidino or morpholino.

3. A compound of claim 1 wherein the A, B, C and D rings contain an 3-OH or protected 3-OH and contain an 12-OH or protected 12-OH and 11- or 12-keto or protected 11- or 12-keto and R is selected from the group consisting of hydroxy, methoxy, ethoxy and morpholino.

4. A compound of claim 1 selected from the group consisting of 5β-4-[3α-(acetyloxy)-11,23,24-trioxo-cholan-24-yl]morpholine, (3α-, 5β)-cholan-3α-ol-11,23-dione-24-oic acid, methyl ester of 5β-cholan-3α-ol-11,23-dione-24-oic acid and 3α-(acetyloxy)-5β-cholan-11,20-dione-24-oic acid.

5. A process for the preparation of a compound of the formula

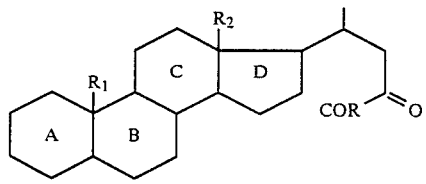

wherein $R_1$ is hydrogen or methyl, $R_2$ is methyl or ethyl, the A, B, C and D rings being saturated or containing at least one double bond and unsubstituted or substituted with at least one member of the group consisting of OH, protected —OH, =O, protected =O, alkyl and alkoxy of 1 to 4 carbon atoms, halogen and alkenyl and alkynyl of 2 to 4 carbon atoms, R is selected from the group consisting of halogen, —OH, alkylthio and alkoxy of 1 to 6 carbon atoms, aralkoxy, arylthio and aralkylthio of 7 to 15 carbon atoms and

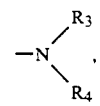

$R_3$ and $R_4$ are individually hydrogen, or alkyl or 1 to 6 carbon atoms or aralkyl of 7 to 15 carbon atoms or taken together with the nitrogen form a heterocycle, which may contain another nitrogen or oxygen atom, excepting the product in which R is methoxy, $R_1$ and $R_2$ each represent methyl, A ring carries a 3β-acetoxy function and B ring contains a double bond in 5(6) comprising reacting a compound of the formula

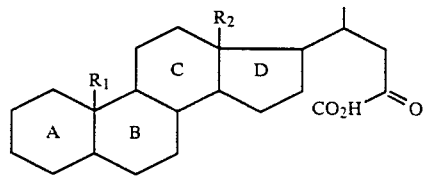

II wherein A, B, C, D, $R_1$ and $R_2$ have the above definitions with a reagent to form the acid halide, then with a tertiary base, then with thionyl chloride and then with a member of the group consisting of water, alkanol, aralkanol, alkylthio, arylthio, aralkylthiol and

wherein $R_3$ and $R_4$ have the above definitions to form a compound of the formula

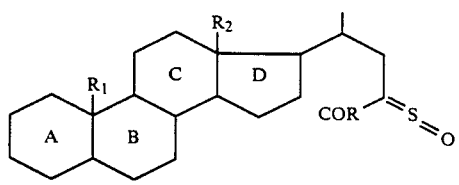

III wherein A, B, C, D, R, R₁ and R₂ have the above definitions and reacting the latter with a halogenation reagent, then with a basic hydrolysis agent and when R is —OH, with a reactant to form the acid halide, alkanol, aralkanol, alkylthiol, arylthiol, aralkylthiol or

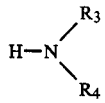

wherein R₃ and R₄ have the above definitions to obtain the corresponding compound of formula I.

6. A process of claim 5 wherein the agent to form the acid halide is thionyl chloride.

7. A process for the preparation of a compound of the formula

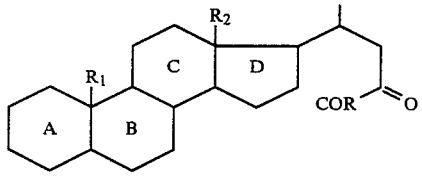

wherein R₁ is hydrogen or methyl, R₂ is methyl or ethyl, the A, B, C and D rings being saturated or containing at least one double bond and unsubstituted or substituted with at least one member of the group consisting of —OH, protected —OH, =O, protected =O, alkyl and alkoxy of 1 to 4 carbon atoms, halogen and alkenyl and alkynyl of 2 to 4 carbon atoms, R is selected from the group consisting of halogen, —OH, alkylthio and alkoxy of 1 to 6 carbon atoms, aralkoxy, arylthio and aralkylthio of 7 to 15 carbon atoms and

R₃ and R₄ are individually hydrogen, or alkyl of 1 to 6 carbon atoms or aralkyl of 7 to 15 carbon atoms or taken together with the nitrogen form a heterocycle, which may contain another nitrogen or oxygen atom, excepting the product in which R is methoxy, R₁ and R₂ each represent methyl, A ring carries a 3β-acetoxy function and B ring contains a double bond in 5(6) comprising reacting a compound of the formula

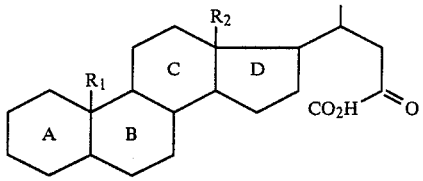

wherein A, B, C, D, R₁ and R₂ have the above definitions with a reagent to form the acid halide, then with a tertiary base, then with thionyl chloride and then with a member of the group consisting of water, alkanol, aralkanol, alkylthiol, arylthiol, aralkylthiol and

wherein R₃ and R₄ have the above definitions to form a compound of the formula

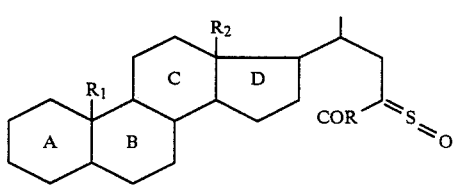

wherein A, B, C, D, R, R₁ and R₂ have the above definitions and reacting the latter with a basic hydrolysis agent and when R is —OH, with a reactant to form the acid halide, alkanol, aralkanol, alkylthio, arylthiol, aralkylthiol or

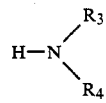

wherein R₃ and R₄ have the above definitions to obtain the corresponding compound of formula I.

* * * * *

UNITED STATES PATENT AND TRADEMARK OFFICE
CERTIFICATE OF CORRECTION

PATENT NO. : 4,927,921

DATED : May 22, 1990

INVENTOR(S) : MICHEL VIVAT and JEAN BUENDIA

Page 1 of 2

It is certified that error appears in the above-identified patent and that said Letters Patent is hereby corrected as shown below:

Col. Line 40  "  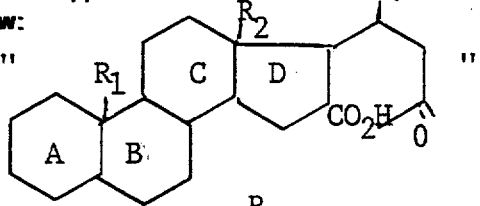  "  should be

-- 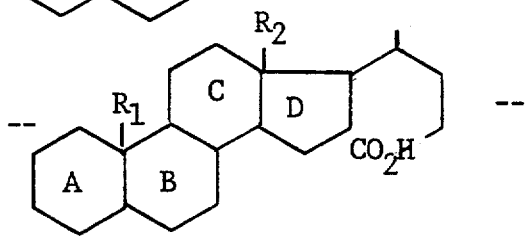 --

UNITED STATES PATENT AND TRADEMARK OFFICE
CERTIFICATE OF CORRECTION

PATENT NO. : 4,927,921

DATED : May 22, 1990

INVENTOR(S) : MICHEL VIVAT and JEAN BUENDIA

It is certified that error appears in the above-identified patent and that said Letters Patent is hereby corrected as shown below:

Col. Line 5 " 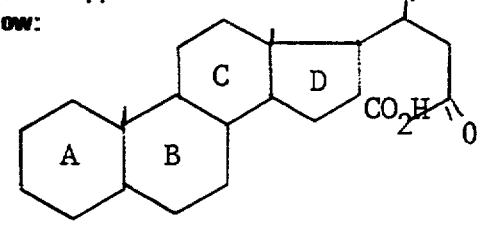 "

claim 7 should be

-- 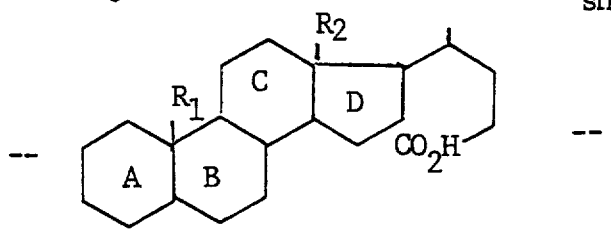 --

Signed and Sealed this

Twentieth Day of September, 1994

*Attest:*

BRUCE LEHMAN

*Attesting Officer*    *Commissioner of Patents and Trademarks*